United States Patent [19]
Schnell et al.

[11] Patent Number: 5,980,741
[45] Date of Patent: Nov. 9, 1999

[54] BUBBLE TRAP WITH FLAT SIDE HAVING MULTIPURPOSE SUPPLEMENTAL PORTS

[75] Inventors: William J. Schnell, Livertyville, Ill.; David S. Utterberg, Seattle, Wash.

[73] Assignee: Medisystems Technology Corporation, Las Vegas, Nev.

[21] Appl. No.: 09/203,013

[22] Filed: Dec. 1, 1998

Related U.S. Application Data

[63] Continuation of application No. 08/905,245, Aug. 1, 1997, abandoned.

[51] Int. Cl.$^6$ .............................. B01D 19/02; A61M 1/00
[52] U.S. Cl. .......................... 210/188; 96/176; 137/583; 210/198.1; 604/4; 604/122; 604/30
[58] Field of Search ..................................... 210/188, 194, 210/198.1, 436; 95/260; 96/155, 176, 179; 137/583; 922/44–48; 604/4, 30, 186, 122, 123, 80, 246

[56] References Cited

U.S. PATENT DOCUMENTS

| | | |
|---|---|---|
| 3,287,885 | 11/1966 | Sommer . |
| 3,342,019 | 9/1967 | Smythe . |
| 3,527,572 | 9/1970 | Urkiewicz . |
| 3,795,088 | 3/1974 | Esmond . |
| 3,908,653 | 9/1975 | Kettering . |
| 3,996,027 | 12/1976 | Schnell et al. . |
| 4,031,891 | 6/1977 | Jess . |
| 4,048,995 | 9/1977 | Mittleman . |
| 4,137,160 | 1/1979 | Ebing et al. . |
| 4,293,413 | 10/1981 | Schnell . |
| 4,311,137 | 1/1982 | Gerard . |
| 4,345,999 | 8/1982 | Sigdell et al. . |
| 4,493,705 | 1/1985 | Gordon et al. . |
| 4,531,937 | 7/1985 | Yates . |
| 4,568,333 | 2/1986 | Sawyer et al. . |
| 4,622,032 | 11/1986 | Katsura et al. . |
| 4,643,713 | 2/1987 | Viitala . |
| 4,666,598 | 5/1987 | Heath et al. . |
| 4,681,606 | 7/1987 | Swan, Jr. et al. . |
| 4,722,725 | 2/1988 | Sawyer et al. . |
| 4,722,731 | 2/1988 | Vailancourt . |
| 4,734,269 | 3/1988 | Clarke et al. . |
| 5,061,236 | 10/1991 | Sutherland et al. . |
| 5,061,365 | 10/1991 | Utterberg . |
| 5,204,000 | 4/1993 | Steadman et al. . |
| 5,228,889 | 7/1993 | Cortial et al. . |
| 5,328,461 | 7/1994 | Utterberg . |
| 5,356,376 | 10/1994 | Milijasevic et al. . |
| 5,358,481 | 10/1994 | Todd et al. . |
| 5,411,705 | 5/1995 | Thor et al. . |
| 5,429,595 | 7/1995 | Wright, Jr. et al. . |
| 5,441,636 | 8/1995 | Chevallet et al. . |
| 5,520,640 | 5/1996 | Utterberg . |
| 5,591,251 | 1/1997 | Brugger . |
| 5,605,540 | 2/1997 | Utterberg ................................. 604/80 |
| 5,683,355 | 11/1997 | Fini et al. . |
| 5,830,185 | 11/1998 | Block ..................................... 604/122 |

FOREIGN PATENT DOCUMENTS

| | | |
|---|---|---|
| 0 058 325 | 8/1982 | European Pat. Off. . |
| 0 318 993 | 6/1989 | European Pat. Off. . |
| 0 350 675 | 1/1990 | European Pat. Off. . |
| 0 587 251 A1 | 3/1994 | European Pat. Off. . |
| 1 408 319 | 10/1975 | United Kingdom . |
| 1 554 810 | 4/1979 | United Kingdom . |

OTHER PUBLICATIONS

Medisystems Sales Drawing of Ready Set™ Bloodtubing Mar., 1993.

*Primary Examiner*—Joseph W. Drodge
*Attorney, Agent, or Firm*—Gerstman, Ellis & McMillin, Ltd.

[57] ABSTRACT

A flow through bubble trap for fluid flow lines comprises a chamber having a substantially flat, lateral side, a first port tube, and a second, opposed port tube. A flow directing baffle system is positioned in the chamber to direct incoming fluid from one of the port tubes into a first, lateral flow direction to allow substantially horizontal fluid flow circulation in the chamber. Fluid flow from the circulating fluid in the chamber enters into the other of the port tubes in a lateral flow direction that is generally the same as the first lateral flow direction, while the baffle system prevents direct flow between the first and second port tubes. The chamber is adaptable to fit with a large variety of conventional dialysis machines and the like, having multi-purpose supplemental access ports, for a simplification of the number of codes necessary for product distribution.

22 Claims, 2 Drawing Sheets

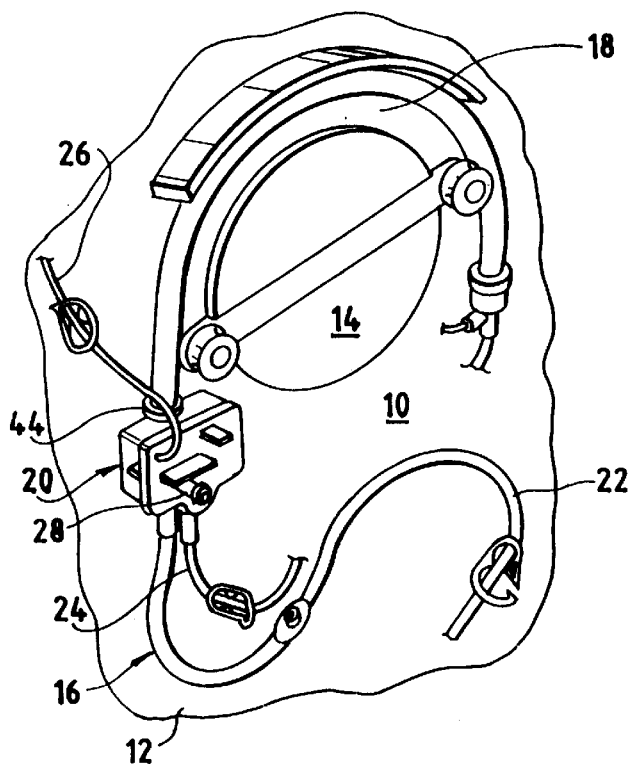
FIG. 1
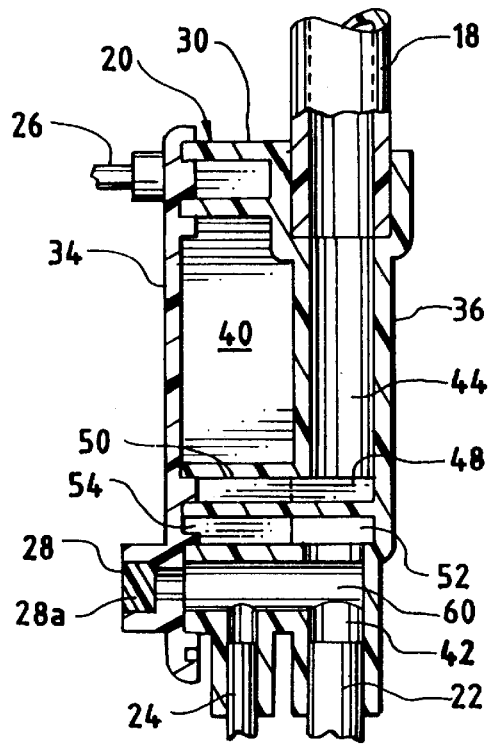
FIG. 3
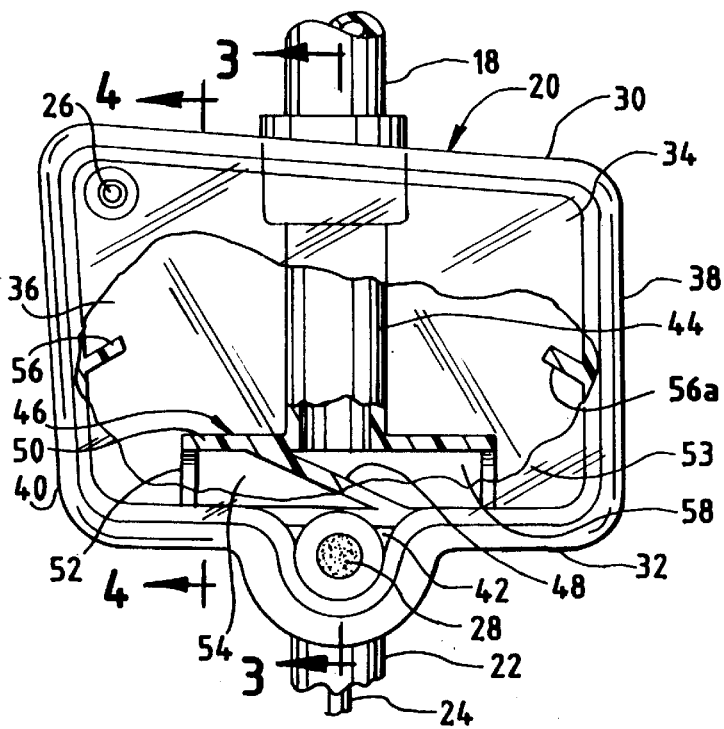
FIG. 2
FIG. 4

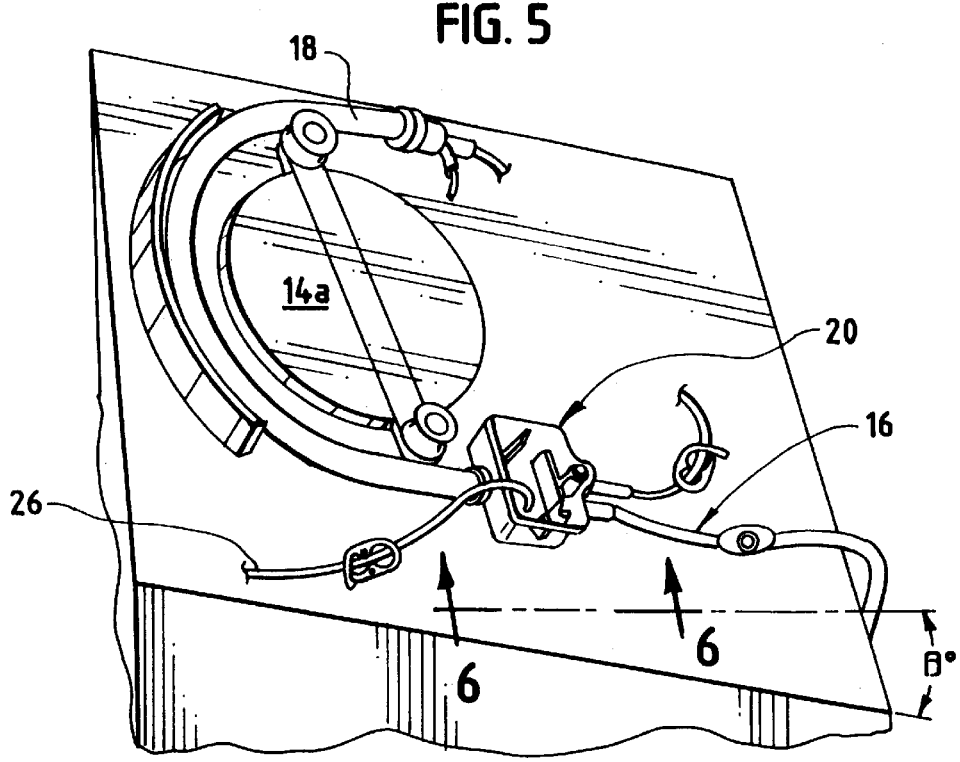
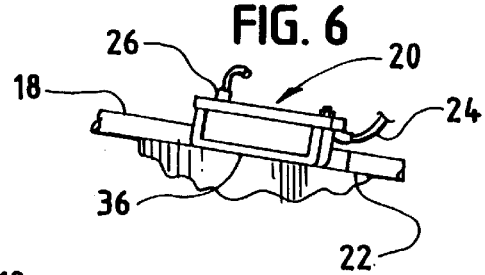
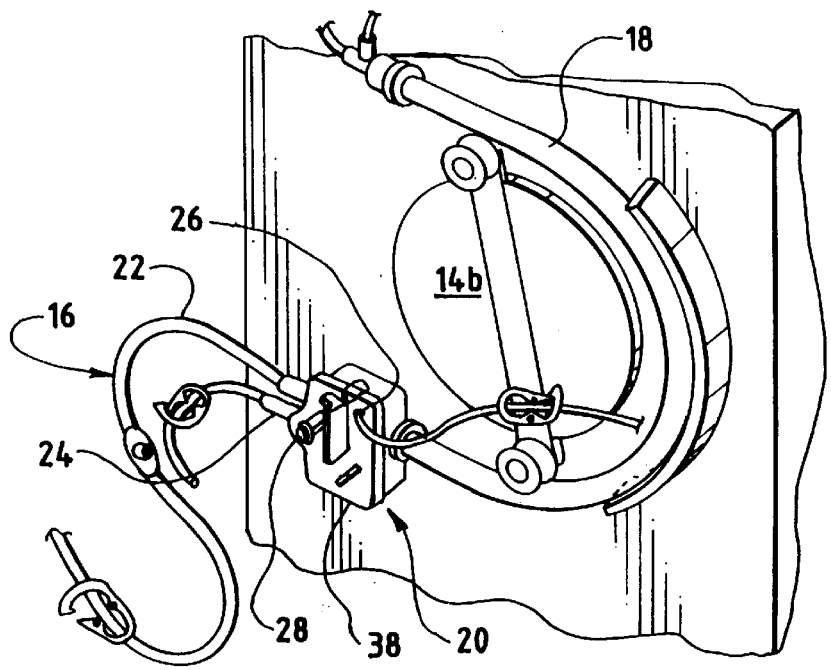

BUBBLE TRAP WITH FLAT SIDE HAVING MULTIPURPOSE SUPPLEMENTAL PORTS

CROSS REFERENCE TO RELATED APPLICATION

This is a continuation of application Ser. No. 08/905,245 filed Aug. 1, 1997, now abandoned.

BACKGROUND OF THE INVENTION

Chambers for blood sets are commonly used in most or all blood sets for the prime purpose of removing gas bubbles from the blood. Such gas bubbles can interfere with the operation of dialyzers, and can be injurious to a patient if allowed to return to the arteriovenous system of the patient.

Conventional bubble traps comprise a typically rigid or semi-rigid tube in which a blood inlet is provided to convey blood into the top of the chamber, while a blood outlet draws blood from the bottom of the chamber. Bubbles are thus given the opportunity to rise to the top of the chamber so that the blood in the bottom of the chamber, which is withdrawn to pass through another portion of the blood set, is relatively free of bubbles, since they migrate to the top of the chamber.

See also Utterberg U.S. Pat. Nos. 5,328,461 and 5,520,640 as other examples of bubble traps for blood lines known to the prior art.

Typically, such bubble traps are taller than they are wide, to provide a deep, vertical chamber for the blood so that bubbles are kept away from the bottom of the chamber from which the blood is being withdrawn.

The inlets of the prior art bubble chambers are variably positioned, the idea being that the blood entering into such inlets, and the bubbles contained in the blood, will initially stay in an upper portion of the chamber so that the bubbles have time to migrate upwardly through a liquid level to a gas space at the top of the chamber. Some inlets are vertically oriented, extending downwardly from the top of the chamber. Because of the height of the chamber, inflowing blood stops moving downwardly before the bubbles contained in it can be caught in the outlet flow. Other inlets of the prior art are vertically oriented in the bottom of the chamber, to propel the inlet blood upwardly toward the chamber top. Other inlets are horizontally oriented in the side of the chamber, so that the inlet flow must horizontally cross the downward flow of the bulk blood in the chamber, moving to an opposite sidewall where it is turned upwardly. This raises the possibility of bubbles being entrained in the downward flow before they are turned upwardly to reach the intended air space.

The bubble trapping principles of the prior art are effective with large, buoyant bubbles, typically having a volume greater than 50 microliters, and at relatively low flow rates of less than 300 ml. per minute. Blood chambers for trapping bubbles typically have volumes of about 15–25 ml. The buoyancy of the bubbles typically urges them to the surface at a velocity greater than the downward velocity of the bulk flow of the fluid in the bubble trap.

However, such bubble traps are increasingly ineffective as bubbles get smaller, and/or as flow rates increase. Modern dialysis techniques often require blood flow rates exceeding 450 ml. per minute, which raises the risk that bubbles can get through bubble traps of the prior art.

To accommodate such higher flows, the volumes of some designs of prior art bubble traps have been increased. However, this is distinctly undesirable, since that increases the priming volume of the set. It is highly desirable to keep the priming volume of any blood set low, since it is important to minimize the amount of blood removed from a patient at any one time during a blood treatment procedure such as dialysis.

In a previous patent application by the applicants, wide bubble traps are disclosed in which the width of the bubble trapping chamber is preferably wider than the height of the chamber. The fluid inlet and fluid outlet to these chambers are then laterally spaced from each other to provide a fluid flow pattern which is substantially horizontal in nature, with less of a vertical flow component than in the prior art. This has been found to facilitate the migration of bubbles upwardly to the top of the chamber.

In other work by the applicants of this application, a bubble trap chamber, specifically shown to be cylindrical, contains a central inlet/outlet tube which serves as the inlet from one end and the outlet from the other end, having side apertures and a partition between the apertures to block direct flow between the inlet portion and the outlet portion of the tube.

However, there remains a need for a bubble trap which can be carried by a large variety of different dialysis machines, to greatly reduce the designs of blood sets that a manufacturer must produce and retain in inventory. Such a flow-through bubble trap is provided by this invention, while exhibiting the many advantages of substantially horizontal flow circulation in the chamber of the bubble trap. Substantial cost savings can be achieved, because the particular design of this invention can be used with a large variety of dialysis machines made by different manufacturers, to greatly reduce the numbers of designs that must be manufactured in order to keep a complete inventory. Also, the bubble traps of this invention can be directly connected to pump tubing to achieve further economies in the field of reduction of the amount of tubing material necessary to manufacture sets in accordance with this invention.

DESCRIPTION OF THE INVENTION

In accordance with this invention a flow-through bubble trap for fluid flow lines is disclosed. Such a bubble trap is typically provided as a component of arteriovenous blood sets for dialysis or any other blood processing procedure, where blood flows through the bubble trap by first entering and then exiting it, leaving gas bubbles behind. Also, the bubble trap can be used as a convenient site for the access of auxiliary branch lines, which may connect to pressure monitors, sources of IV solution, sources of heparin or the like.

By this invention, the bubble trap defines a chamber having top, bottom and side walls. The chamber, in turn, defines a substantially flat, lateral side, which can be placed next to any of a variety of dialysis machines with a good operating fit. Examples of such dialysis machines are many of the models sold by Fresenius, Althin, and Baxter International. Thus, since a single set can be used in conjunction with all of these different designs, a great reduction in the number of models or codes for the sets can be achieved.

A first port tube communicates upwardly into the chamber, typically through the bottom wall. A second port tube communicates downwardly into the chamber, typically through the top wall. A flow-directing system may preferably be positioned adjacent to the bottom wall, to direct incoming fluid from one of the port tubes, typically the bottom port tube for "prepump" chamber location or the top port tube for "postpump" chamber location, into a first, lateral flow direction relative to the direction of flow within the port tubes. From there, the flowing fluid enters into a substantially horizontal fluid flow circulation in the chamber, exhibiting only a relatively minor vertical flow component, contrary to many chambers of the prior art.

The flow directing system also allows fluid flow from the circulating fluid in the chamber to flow into the other of the port tubes in a lateral flow direction that is generally the same direction as the first lateral flow direction, while preventing direct flow between the first and second port tubes.

Preferably, the chamber of this invention has substantially rectangular sidewalls, plus a horizontal width that is at least as great as the height of the chamber and preferably greater than the chamber height. This causes the circulating flow within the chamber to be mostly horizontal in nature. The horizontal thickness or depth of the chamber of this invention is preferably less than both the horizontal width thereof and the height of the chamber. The chamber may have a width on the order of 4 or 5 cm. and an internal volume which is preferably no more than about 25 cc.

At least one and typically both of the port tubes are positioned closely adjacent to the flat, lateral side described above, which facilitates fitting of the chamber on a wide variety of dialysis machines. That port tube positioned adjacent to the flat, lateral side may directly connect to a length of roller pump tubing without the need for an intermediate length of flow tubing. This provides an added economy by eliminating such an intermediate length of tubing.

The sidewalls preferably carry at least one inwardly extending, generally horizontal vane to slow the vertical flow component of the substantially horizontal flow circulation. This can further reduce the number of microbubbles of gas which escape through the bubble trap into the outlet flow of blood.

The flow directing system of this invention may comprise an angled wall as a baffle, which is positioned between the first and second port tubes to prevent their direct flow connection with each other. The baffle system may further comprise horizontal wall portions to direct incoming fluid laterally. Thus, blood enters the bubble trap chamber and is directed to one lateral side, preferably along its longest lateral dimension. From there, the blood circulates through essentially the entire lateral width of the major side of the bubble trap, being collected into a passageway from a position adjacent to the opposed lateral side of the chamber. This maximizes the time of horizontal blood flow, which, in turn, gives maximum time for microbubbles to rise to the top of the chamber, where they may be trapped.

The chamber of this invention may also carry other ports for connection with branch tubing which may connect to a pressure monitor device, a source of saline solution and/or heparin, and the like. Particularly by this invention, a pressure monitor port may be provided on the respective chamber to communicate with the "highest" portion of the enclosed volume within the chamber irrespectively of whether the chamber is oriented with its back wall in a vertical position, a downwardly facing position, or rotated laterally by approximately 90° while remaining vertical.

In another aspect of this invention, it is typical in the current art to have an array of access ports carried on blood sets, comprising injection sites and/or branch lines communicating with the set for the administration of medicaments or obtaining blood samples. Prior art injection sites and branch lines appear on main tubes, chamber top caps, chamber walls, or on the IV priming set.

Often, a typical arterial or venous blood tubing set will have three or more access ports. This is due to the variety of modalities of administration and sampling, being influenced by the following factors;

(a) Some medication administrations need to be directly administered into the bloodstream.

(b) Some drugs are more toxic, and must be diluted to lower concentrations with IV fluids before entering the bloodstream.

(c) Other expensive, low volume drugs must be administered directly to the blood, followed by a "saline flush" to assure that all of the drug reaches the blood stream.

(d) Arterial blood samplings need to taken upstream of the flow-through treatment device, typically a hemodialyzer.

(e) Venous samplings need to be taken upstream of the bubble trap chamber.

(f) Viscous or clot-enhancing administrations must be given on the venous side downstream of the hemodialyzer.

(g) Expensive, low volume drugs must be administered downstream of the venous bubble trap chamber, if said chamber has any stagnant areas that would impede delivery of the drug to the patient.

In the prior art, access ports such as injection sites on the main tubes are suitable for simple drug delivery or blood sampling as the injection sites directly access the blood stream. However, such injection sites are not suitable for diluting drugs or following drug administration with a saline flush. For these modalities, the prior art places an injection site on the IV administration tube away from the blood flow tubing. Of course, this makes such injection sites unsuitable for blood sampling. Furthermore, injection sites on the chamber top caps are suitable for fluid administration, but not for sampling, as the site is adjacent an air space above the blood. Thus, prior art blood tubing sets are equipped with many different kinds of access ports to handle the variety of modalities.

As is well known, however, during most dialyses, most or all of these ports and tubings are not required. Thus, a substantial portion of the cost of manufacturing blood tubing sets is for access ports that are used very infrequently for occasional or emergency use only. It is therefore highly desirable in today's cost-driven medical environment to reduce the number of access ports on blood tubing sets without reducing the physician's ability to perform necessary administrations or samplings on any of the modalities required.

By this invention, such a reduction can be achieved. This can be accomplished with a flow-through bubble trap having a main chamber and first and sealed port tubes communicating with the main chamber for main fluid flow therethrough. A central manifold is provided which communicates with one of the port tubes adjacent to the chamber. A plurality of auxiliary ports communicate with the central manifold. The auxiliary ports comprise an injection port positioned on the manifold so that an injection needle can penetrate through the injection port and extend into the main fluid flow of the one port tube. Another of the auxiliary ports typically communicates with the length of flexible tubing for connection with a source of intravenous solution.

By such an arrangement, most or all of the various types of medicament administration and blood sampling can be achieved, with the use of only two access ports, although more access ports may be provided if desired.

DESCRIPTION OF THE DRAWINGS

Referring to the drawings, FIG. 1 is a fragmentary, perspective view showing an arterial blood set for hemodialysis carried on a roller pump of a conventional dialysis machine with the chamber of this invention;

FIG. 2 is an enlarged, elevational view of the chamber of this invention with portions broken away;

FIG. 3 is a sectional view taken along line 3—3 of FIG. 2;

FIG. 4 is a sectional view taken along line 4—4 of FIG. 2;

FIG. 5 is a perspective view of the arterial blood set of FIG. 1, inserted into a different roller pump which is substantially horizontally positioned;

FIG. 6 is an elevational view of the arrangement of FIG. 5; and

FIG. 7 is a perspective view of the blood set of FIG. 1 installed in another roller pump set which is rotated about 90° from the roller pump of FIG. 1, so that the roller pump tubing is inserted laterally into the roller pump.

DESCRIPTION OF SPECIFIC EMBODIMENTS

Referring to the drawings, a conventional dialysis machine 10 is shown having a face plate 12 through which a roller pump 14 projects. An arterial set for hemodialysis 16 is provided, being of generally conventional construction except as otherwise indicated herein. Arterial set 16 carries conventional roller pump tubing 18 fitted into the roller pump 14 in a conventional manner.

Roller pump tubing 18 connects with a flow-through bubble trap chamber 20 in accordance with this invention. Bubble trap chamber 20, in turn, has several ports that respectively connect with the main flow tubing 22 of arterial set 16 and branch connection lines 24, 26, which may be conventional in design per se, and are provided for the purpose of connection with a pressure monitor, a source of IV solution, a source of heparin, or the like. Chamber 20 can also carry an aperture 28 which is filled with an elastomer-type resealable injection site.

Branch connection line 26 and the corresponding port communicates with chamber 20 and serves as the pressure monitor port and line. The line and port 26 communicate with the "highest" portion of the volume enclosed in chamber 20 when back wall 36 is in the vertical position as shown, but also if back wall 36 is in a substantially horizontal position as in FIGS. 5 and 6, or if chamber 20 is rotated so that sidewall 38 is the lowest wall in the position of use of chamber 20, as in FIG. 7.

If the roller tubing 18 rotates clockwise in direction, chamber 20 is in a "pre-pump" location, and blood flows from main flow tubing 22 to roller tubing 18. Pressures in the chamber are then typically negative, and port 24 is typically a source for IV solution administration. If roller tube 18 rotates counterclockwise, chamber 20 is in a post-pump location. Flows proceed from roller tubing 18 to main flow tubing 22. Pressures then are typically positive in chamber 20.

FIG. 2 shows chamber 12 to be substantially, but not exactly, rectangular in shape, having a top wall 30, a bottom wall 32, opposed major sidewalls 34, 36 and opposed minor sidewalls 38, 40. It can be seen that chamber 20 is wider than it is tall, so that the flow circulation through the chamber is substantially horizontal, with only a relatively minor vertical flow component.

Chamber 20 defines a first port 42 that communicates upwardly into the chamber. Chamber 20 also defines a second port 44 that communicates downwardly into the chamber, passing through upper wall 30, as first port 42 extends through lower wall 32.

A flow-directing baffle system 46 is provided adjacent to bottom wall 32, to direct incoming fluid from one of the port tubes 42, 44 into a first lateral flow direction. Specifically, the baffle system 46 comprises an angled wall 48 positioned between the top of first port tube 42 and the bottom of second port tube 44. Baffle system 46 also comprises horizontal wall portions 50, through which second port 44 passes, and which portions 50 connect with angled wall 48. The sides or ends 52, 53 under horizontal wall 50 are open to the interior of chamber 20, while walls 48, 50 extend to join (as a part of or abutting against) major sidewalls 34, 36. Sidewall 36 may comprise the flat back wall previously discussed, which permits installation of the chamber of this invention into a large variety of hemodialysis machines.

Flow-through chamber 20 can pass flow in either direction with substantially similar results. If the flow is upward, with first port tube 42 connected to and receiving blood from set tube 22, the blood rises upwardly into the first space 54, defined by the lower surface of angled wall 48 and a portion of horizontal wall 50, to flow to the left through open side or end 52 in a horizontal manner, and thus to enter into circulating flow within chamber 20. The upward motion of such blood in circulating flow is restricted but not eliminated by the presence of horizontal vane 56, which is carried by minor sidewall 40.

Blood is then withdrawn from chamber 20 through a passageway 58 defined by the upper surface of angled wall 48 and a right hand portion of horizontal wall 50, blood being drawn in from the open side or end 53 from the circulating flow of blood within the chamber, to be drawn upwardly through second port tube 44, and from there into roller pump tubing 18, which is conventionally attached to second port tubing 44. Second horizontal vane 56a is provided to further restrict but not eliminate the vertical flow component in the chamber.

If flow is in the other direction, initially from roller pump tubing 18 into second port tube 44, the pattern of flow is in the opposite direction, with similar bubble removing characteristics, with the flowing blood passing downwardly through first port tube and out along set tubing 22.

Since the major portion of the flow component of this chamber is preferably horizontal rather than vertical, improvements are achieved in the removal of bubbles from blood, including microbubbles. Such bubbles and microbubbles migrate to the top of the chamber where they reside until removed, for example by removal through the tube 26 and the aperture of the chamber which retains such tube.

It can be seen from FIG. 3 that roller pump tubing 18 and second port tube 44 are positioned along rear sidewall 36 of the chamber. This facilitates the fitting of sets carrying the chamber of this invention with a larger number of commercially available hemodialysis machines, so that the number of different designs and codes of respective arterial (and venous) sets using the chamber of this invention may be reduced.

Though terms such as "up", "down", "height" and "width" have been used to define the chamber in the orientation of FIGS. 1–4, it is a feature of this invention that it can be successfully operated in other orientations as well. For example, FIG. 5, in which the chamber works with a conventional blood pump 14a that is essentially horizontal rather than vertical. In this orientation, the back wall 36 of FIGS. 3–4 becomes bottom wall 36 of FIG. 5. The flows in chamber 20 of FIGS. 5–6 are still primarily horizontal rather than vertical, so that the chamber functions as described above for the original orientation.

Thus, this chamber may be used on dialysis machines in which the roller pump is substantially horizontal.

Some other machines have blood pumps with a vertical orientation, but with the pump's opening turned to the side. In FIG. 7, pump 14b shows this orientation. Chamber 20 here is positioned on its side such that the sidewall 38 of FIG. 2 becomes the bottom wall 38 of FIG. 7. Monitor tubing and port 26 of FIG. 2 remains the monitor tubing in the same port of the FIG. 5 and FIG. 7 embodiments. The monitor tubing in port 26 still communicates with the highest point in the chamber, and thus is unlikely to pick up blood from the chamber. However, air can be vented through this port and tubing 26 as desired.

The chamber of this invention defines a central manifold passage 60, which serves as a plenum for the mutual connection of injection site port 28, branch or auxiliary tubing 24 (and the port to which it is attached), and first port tube 42, so that they all can connect with space 54. Space 54, in turn connects with the main portion of the chamber interior. Tubing 24 may preferably comprise a full priming set of conventional design.

Central manifold 60 and its connecting arrangement with injection site 28, line and port 24 (typically used for priming), and first port tube 42 which connects with line 22 are arranged to permit all of the desired arterial administrations and samplings as described below. Specifically, manifold 60 is substantially cylindrical with injection site 28 positioned at one end and positioned perpendicular to the main flow of fluid through port tube 22 and its connecting port 42.

Thus, a regular medicament may be infused by cannula through injection site 28 directly into the blood stream, with the cannula entering central manifold 60 into main port 42 so as to be in the direct stream of flow. Such a cannula may be a sharp cannula or a blunt cannula in the manner of the blunt cannula described in Utterberg Patent No. 5,071,413. Injection site 28 may carry a solid or a slit elastomer partition 28a, or it may comprise a branch line with a female luer connector, or a stopcock, or any such suitable flow control connection.

A toxic medicament may be infused by a cannula through injection site 28, while simultaneously infusing saline via tubing and port 24. The central manifold 60 allows a dilution space for mixing of the drug with the saline and then the blood.

An expensive or low volume drug may be infused by cannula through injection site 28, followed by a saline flush via saline port 24, which clears any residue drug from central manifold 60 and passes it into the main flow of port 42.

Blood may be sampled by passing a cannula through injection site 28 and central manifold 60 to extend directly into the main flow path for blood in port 42.

If desired, medicament may be administered through solution line 24.

By the above means, the number of access ports required on a blood conveying set can be reduced to two ports, which can serve every needed function of medicament administration and sampling that can be achieved from the particular location.

Branch line 26 may then connect to a pressure sensing monitor.

Most of chamber 20 can be molded in a cup-shaped configuration as shown in FIG. 4. Then, separately molded front wall 34 may be attached and sealed at the molded sealing groove 62, which engages with each of the walls to provide a hermetically sealed chamber except at its various access ports.

The above has been offered for illustrative purposes only, and is not intended to limit the scope of the invention of this application, which is as defined in the claims below.

That which is claimed:

1. A flow-through bubble trap for fluid flow lines, which comprises:
    a main chamber having top, bottom, and sidewalls;
    first and second port tubes communicating with said chamber for main fluid flow therethrough;
    a central manifold that communicates with one of said port tubes adjacent to said chamber;
    a plurality of auxiliary ports that communicate with said central manifold, one of said auxiliary ports comprising an injection port positioned on said manifold so that an injection cannula can penetrate through said injection port and extend into the main fluid flow of the one port tube, another of said auxiliary ports communicating with a length of flexible tubing for connection with a source of intravenous solution, said central manifold being of straight, tubular shape, said injection port being positioned at one end of said tubular shape of the manifold, and the other end of said manifold tubular shape communicating with said one port tube in transverse relation thereto, said another auxiliary port and length of flexible tubing communicating with said manifold in transverse relation thereto, said chamber further defining a flow-directing system positioned to direct incoming fluid from one of said port tubes into a first lateral flow direction, and then to allow substantially horizontal fluid flow circulation in said chamber, said flow-directing system also allowing fluid flow from circulating fluid in said chamber into the other of said port tubes in a lateral flow direction, while preventing direct flow between said first and second port tubes, said flow directing system comprising an angled wall positioned between said first and second port tubes, and in which said flow directing system further comprises horizontal wall portions to direct incoming fluid from one of said port tubes into one lateral side of said chamber, and to define a horizontal passageway extending from an opposed, lateral side of said chamber to convey fluid from said chamber to the other of said port tubes.

2. The bubble trap of claim 1 in which said first port tube communicates upwardly into said chamber and said second port tube communicates downwardly into said chamber.

3. The bubble trap of claim 1 in which said chamber defines a substantially flat, lateral side.

4. The bubble trap of claim 3 in which said chamber has substantially rectangular sidewalls, and a horizontal width that is at least as great as the height of said chamber.

5. The bubble trap of claim 4 in which said chamber has a horizontal thickness that is less than each of said horizontal width and said height.

6. The bubble trap of claim 5 in which at least one of said port tubes is positioned adjacent to said flat, lateral side, and directly connects to a length of roller pump tubing.

7. The bubble trap of claim 6 in which said sidewalls carry at least one inwardly extending horizontal vane to slow the vertical flow component of said substantially horizontal flow circulation.

8. The bubble trap of claim 6 in which said second port tube extends downwardly through said chamber to at least a position near said flow directing system.

9. The bubble trap of claim 4 in which said substantially rectangular sidewalls are varied from exact rectangular shape to cause an upper wall of said bubble trap to exhibit a slight slope toward one upper corner, and a branch connection line communicating with said chamber adjacent to said upper corner.

10. A tubular set for conveyance of blood which comprises flexible tubing connected to the bubble trap of claim 1.

11. A flow through bubble trap for fluid-flow lines, which comprises:
   a main chamber having top, bottom, and sidewalls;
   an inlet port tube and an outlet port tube communicating with said chamber for main fluid flow therethrough;
   a central tubular manifold that communicates with one of said port tubes adjacent to said chamber;
   a plurality of auxiliary ports that communicate with said central manifold, one of said auxiliary ports comprising an injection port positioned on said manifold so that an injection cannula can penetrate through said injection port and extend into the main fluid flow of the one port tube, another of said auxiliary ports communicating with a length of flexible tubing for connection with a source of intravenous solution, said chamber further defining a flow directing system positioned to direct incoming fluid from said inlet port tube substantially exclusively into a first lateral flow direction, and then to allow substantially horizontal fluid flow circulation in said chamber, said flow directing system also allowing fluid flow from circulating fluid in said chamber into the other of said port tubes in substantially the same first lateral flow direction, while preventing direct flow between said inlet and outlet port tubes.

12. The bubble trap of claim 11 in which said central manifold is of straight, tubular shape, said injection port being positioned at one end of said tubular shape of the manifold, and the other end of said manifold tubular shape communicating with one of said port tubes in transverse relation thereto, said another auxiliary port and tubing communicating with said manifold in transverse relation thereto.

13. The bubble trap of claim 12 in which said chamber has substantially rectangular sidewalls, a substantially flat, lateral side, a horizontal width that is at least as great as the height of said chamber, and a horizontal thickness that is less than each of said horizontal width and said height.

14. The bubble trap of claim 13 in which at least one of said port tubes is positioned adjacent to said flat, lateral side, and directly connects to a length of roller pump tubing.

15. The bubble trap of claim 13 in which said sidewalls carry at least one inwardly extending horizontal vane to slow the vertical flow component of said substantially horizontal flow circulation chamber.

16. The bubble trap of claim 13 in which said substantially rectangular sidewalls are varied from exact rectangular shape to cause an upper wall of said bubble trap to exhibit a slight slope toward one upper corner, and a branch connection line communicating with said chamber adjacent to said upper corner.

17. A tubular set for conveyance of blood which comprises flexible tubing connected to the bubble trap of claim 11.

18. A flow through bubble trap for fluid flow lines, which comprises:
   a main chamber having top, bottom and sidewalls;
   first and second port tubes communicating with said chamber for main fluid flow therethrough;
   a central manifold that communicates with one of said port tubes adjacent to said chamber, said central manifold being of straight, tubular shape;
   a plurality of auxiliary ports that communicate with said central manifold, one of said auxiliary ports comprising an injection port positioned at one end of said tubular shape of the manifold, the other end of said manifold communicating with one of said port tubes in transverse relation thereto, so that an injection cannula can penetrate through said injection port and extend into the main fluid flow of the one port tube, another of said auxiliary ports communicating with a length of flexible tubing for connection with a source of intravenous solution, said another auxiliary port and tubing communicating with said manifold in transverse relation thereto.

19. The bubble trap of claim 18 in which said chamber has substantially rectangular sidewalls, a horizontal width that is at least as great as the height of said chamber, and a horizontal thickness that is less than each of the horizontal width and said height.

20. The bubble trap of claim 19 in which said sidewalls carry at least one inwardly extending horizontal vane to slow the vertical flow component of said substantially horizontal flow circulation.

21. The bubble trap of claim 20, in which said substantially rectangular sidewalls are varied from exact rectangular shape to cause an upper wall of said bubble trap to exhibit a slight slope toward one upper corner, and a branch connection line communicating with said chamber adjacent to said upper corner.

22. A tubular set for conveyance of blood which comprises flexible tubing connected to the bubble trap of claim 18.

* * * * *